United States Patent
Stern et al.

[11] Patent Number: 6,079,681
[45] Date of Patent: Jun. 27, 2000

[54] MR COMPATIBLE NEUROSURGICAL POSITIONING APPARATUS

[75] Inventors: Benjamin R. Stern, Willoughby Hills, Ohio; David A. Molyneaux, Gainesville, Fla.; David A. Lampman, Eastlake, Ohio

[73] Assignee: Picker International, Inc., Cleveland, Ohio

[21] Appl. No.: 09/157,347

[22] Filed: Sep. 18, 1998

Related U.S. Application Data

[60] Provisional application No. 60/060,103, Sep. 26, 1997.

[51] Int. Cl.[7] ................................................. E04G 3/00
[52] U.S. Cl. ............................................ 248/278.1; 606/1
[58] Field of Search .............................. 248/274.1, 276.1, 248/278.1, 279.1; 606/1

[56] References Cited

U.S. PATENT DOCUMENTS

| | | |
|---|---|---|
| 4,573,452 | 3/1986 | Greenberg . |
| 5,263,956 | 11/1993 | Nobles . |
| 5,320,444 | 6/1994 | Bookwalter et al. . |
| 5,396,905 | 3/1995 | Newman et al. ........................ 128/849 |
| 5,447,149 | 9/1995 | Kikawada et al. ............... 248/276.1 X |
| 5,597,146 | 1/1997 | Putman ................. 248/276.1 |
| 5,662,300 | 9/1997 | Michelson . |
| 5,748,767 | 5/1998 | Raab ........................ 606/1 X |
| 5,757,189 | 5/1998 | Molyneaux et al. . |
| 5,931,832 | 8/1999 | Jensen .......................................... 606/1 |
| 5,938,599 | 8/1999 | Rasche et al. ........................... 600/410 |

FOREIGN PATENT DOCUMENTS 0 832 611  4/1998  European Pat. Off. .

OTHER PUBLICATIONS

Internet Brochure: "Mayfield®/Acciss™ Image Guided System" revised May 11, 1998; Ohio Medical Instrument Co., Inc. OMI Surgical Products.

Primary Examiner—Ramon O. Ramirez
Attorney, Agent, or Firm—Timothy B. Gurin; John J. Fry; Eugene E. Clair

[57] ABSTRACT

An apparatus (1) for supporting a surgical instrument in the operative environment of an imaging device comprises components all made of a material compatible for use in the operative environment of the imaging device. The components of the apparatus (1), made of such a material, include a member (32) that has a spherical surface and includes a bore (50) extending through the member along its diameter. A grip (26) has a grip surface (40) defining an aperture that is adapted to receive the member for rotatable movement within the aperture. The grip (26) extends around the member (32) in a circumferential path and has a gap (42) therein. A fastener (30) is operatively connected to the grip (26). The fastener (30) is adjustable to change the size of the gap (42) and adjust the compressive force applied to the received member (32) in the grip.

23 Claims, 7 Drawing Sheets

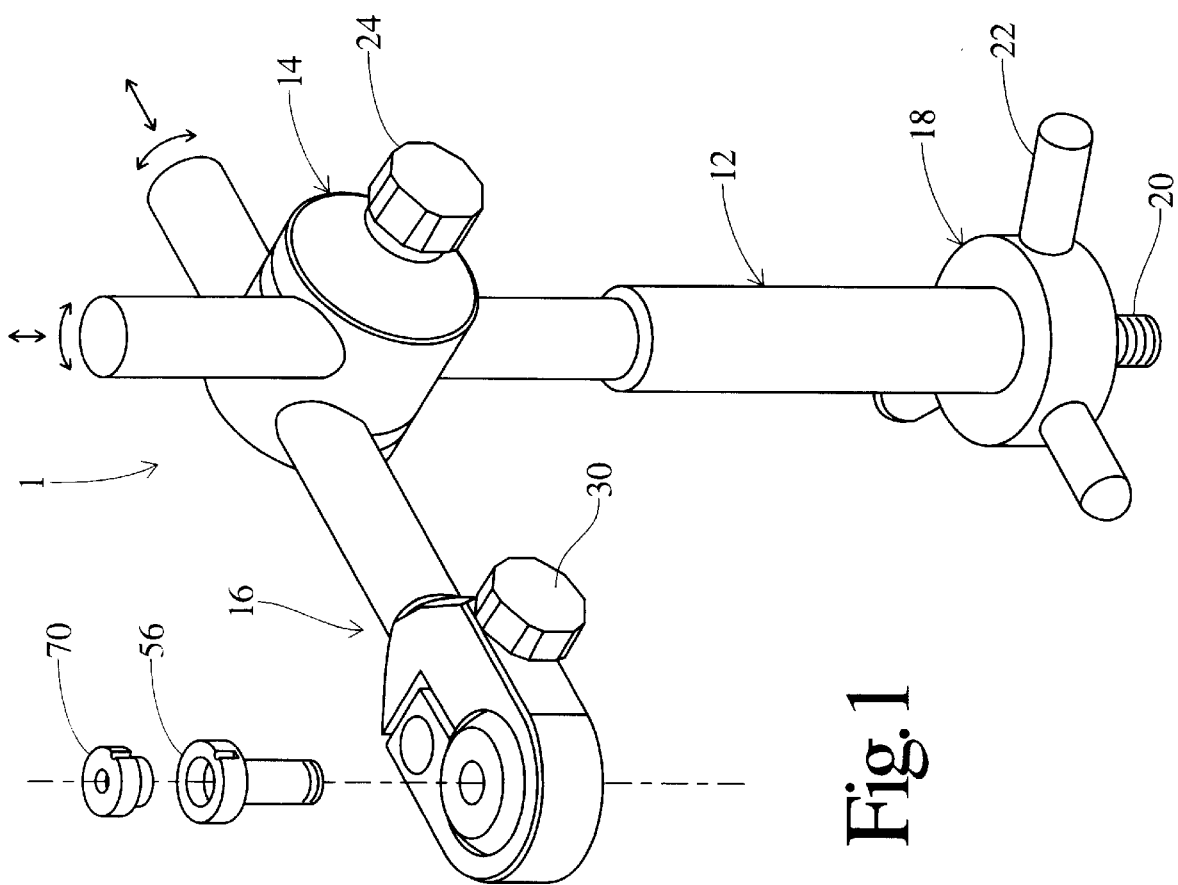

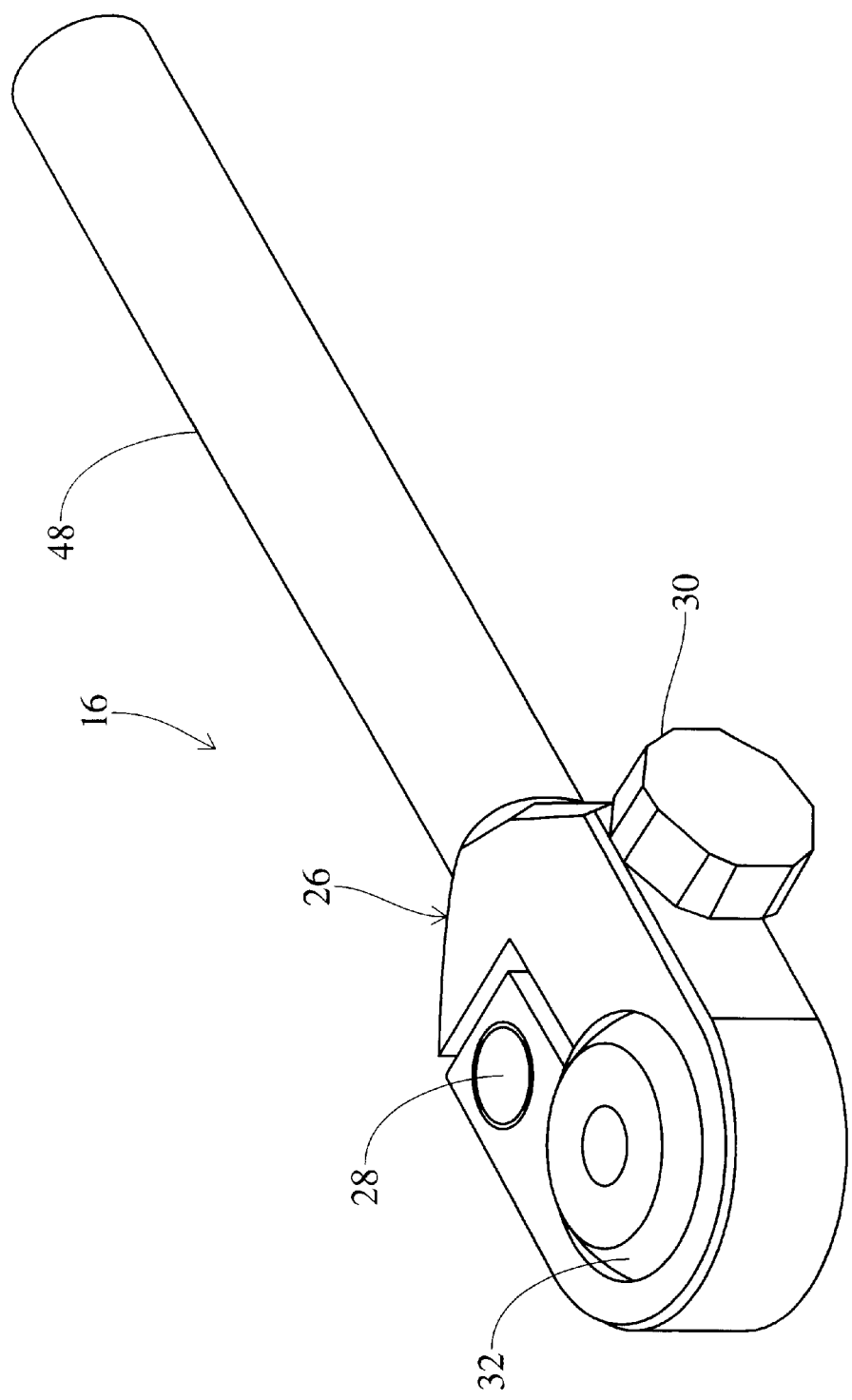

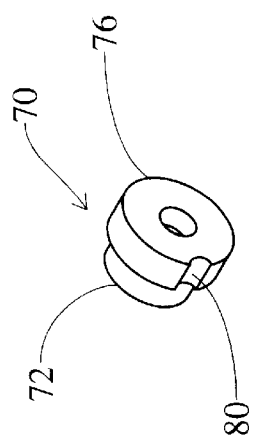
Fig. 8A
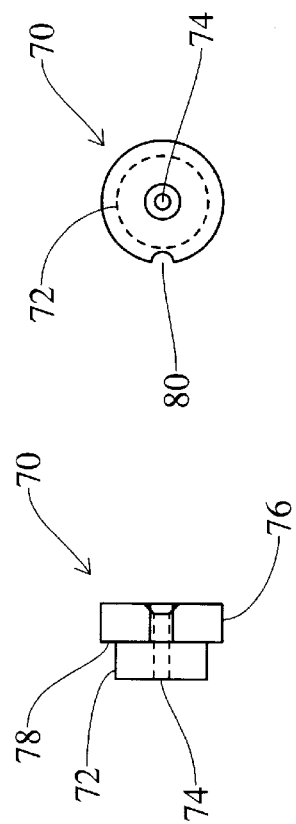
Fig. 8C
Fig. 8B
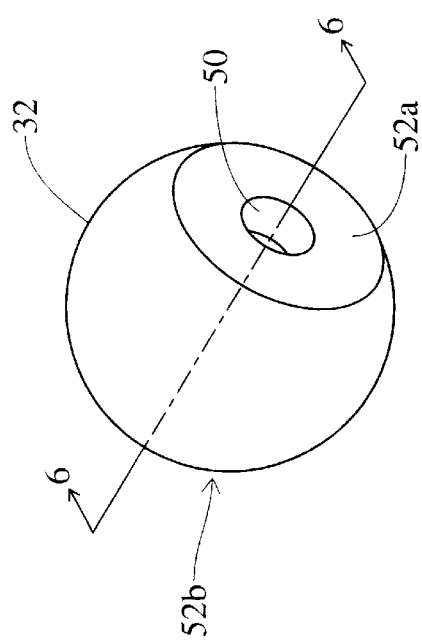
Fig. 5
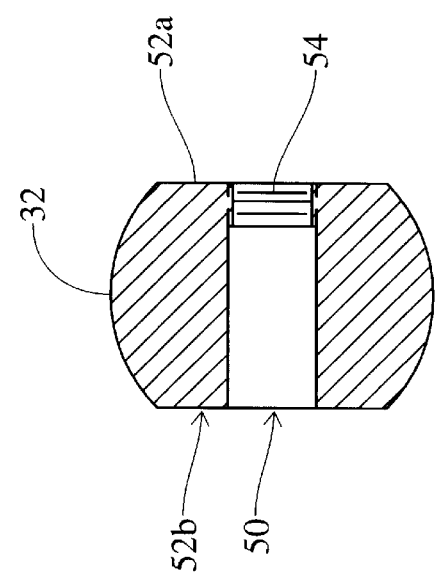
Fig. 6

MR COMPATIBLE NEUROSURGICAL POSITIONING APPARATUS

CROSS REFERENCE TO RELATED APPLICATION

This application claims the benefit of provisional application Ser. No. 60/060,103 filed Sep. 26, 1997, in the name of Stern et al., for MR Compatible Neurosurgical Positioning Apparatus.

BACKGROUND OF THE INVENTION

The present invention relates to the medical diagnostic and surgical arts and is particularly related to a surgical tool support apparatus that is (i) MR-Safe and MR-compatible and/or (ii) X-Ray/CT compatible for use in the operative environment of an imaging modality. The present invention finds particular application in conjunction with neurosurgery and will be described with particular respect thereto. It will be appreciated, however, that the invention finds application in conjunction with biopsies, endoscopic procedures, orthopedic surgeries, other medical procedures, industrial quality control procedures, and the like in which a tool or device must be accurately positioned in relation to an object.

Image guided surgery systems are particularly well adapted to intra-cranial and spinal surgery. These systems use diagnostic images of the patient to assist the physician with presurgical planning and to provide information relating to the position and orientation of the anatomy and instrumentation during a surgical procedure. Image guided surgery systems are well-suited for use in connection with magnetic resonance ("MR") and computerized tomography ("CT") images, as well as with other imaging modalities. well-suited for use in connection with magnetic resonance ("MR") and computerized tomography ("CT") images, as well as with other imaging modalities.

In cranial applications, a patient reference frame may be defined using three or more points fixed in relation to the patient's head. According to one method, at least three markers visible to the imaging device are affixed to the skin prior to imaging. According to another method, anatomical reference points are used. According to a third method, fiducial markers may be affixed to the skull, for example as disclosed in U.S. Pat. No. 4,991,579, Method and Apparatus for Providing Related Images of the Anatomy over time of a Portion of the Anatomy Using Fiducial Implants, to Allen, issued Feb. 12, 1991. Similar techniques may be used to define a patient reference frame with respect to other portions of the anatomy.

An image of the patient having an image reference frame is then obtained. Based on the location of the three or more markers within the image data, the image and patient reference frames can be correlated. Hence, the position of a feature of interest within the image can be determined with respect to the patient reference frame. After image acquisition is complete, the patient can be moved as desired. The patient is subsequently placed in an operating room environment, for example on an operating table.

The patient and operating room reference frames are correlated or "zeroed" by touching the surgical tool to the at least three markers. The position of the tool with respect to the cameras, and hence the position of the markers, is then determined. Inasmuch as the relationship between the patient, operating room, and image frames of reference is known, the position of the tool with respect to the image reference frame can then be determined. Relevant images, with the position of the surgical tool indicated thereon, are then displayed on a monitor. The surgeon is thus provided with a real time indication of the position of the surgical tool with respect to the previously obtained image.

In order to assist in the accurate positioning of surgical tools, neurosurgical procedures such as brain biopsies can be performed using a positioning apparatus such as a surgical guide. The surgeon uses the image guided surgery system to assist in positioning and orienting the guide. The guide is used to guide a biopsy needle or other surgical instrument along the desired trajectory.

Greenberg and Bookwalter clamps marketed by Johnson and Johnson Professional, Inc, a subsidiary of Johnson and Johnson, as part of their Codman line of surgical instruments, have been used as positioning devices for surgical procedures. These devices consist of a series of links that are held in compression by a cable going through the centers of the links, forming a pre-loaded gooseneck mechanism. A clamping mechanism at the lower end of the devices attaches to the operating table or to the patient restraint apparatus. A clamping mechanism at the upper end of the devices holds the surgical instrument. Several reducing tubes of different sizes are used to adapt the devices to hold different instruments. Designs of gooseneck-type surgical positioning devices are described in U.S. Pat. Nos. 4,573,452 by Greenberg, 5,662,300 by Michelson. Use of a ball joint in a surgical positioning device is described in U.S. Pat. No. 5,320,444 by Bookwalter.

It is becoming increasingly desirable to perform MR-guided or MR-assisted interventional surgical procedures, which are ordinarily conducted in the immediate vicinity of a magnetic resonance imaging scanner. These procedures require, however, that the equipment used be MR-safe, meaning that it will not be adversely affected by the magnetic and electric fields of the scanner. Furthermore, to perform such procedures inside the imaging volume of an MRI scanner without degradation of the scanner's imaging performance, the devices must be MR-compatible, meaning that they do not disturb the magnetic or electric fields of the scanner, and do not emit MR signals with the imaging sequences being used. For other imaging modalities, such as X-Ray, CT or Fluoroscopic imaging systems, the term compatible indicates that the device is generally transparent in an image when the device is placed in the operating environment of those imaging modalities.

The Greenberg and Bookwalter clamps described above are fabricated from stainless steel. Therefore, they are not MR-compatible as they disturb the homogeneity of the magnetic and electric fields. At the edges of the magnetic field, these devices may experience magnetic forces and thus are not MR-safe. The introduction of an electrically conductive device can introduce eddy currents which deleteriously affect the magnetic fields within the MR scanner. Yet another disadvantage to the introduction of an electrically conductive device is that the likelihood of inadvertent connections or short circuits between electrical devices in the area is increased. As a result, the Greenberg and Bookwalter clamps are not suitable for use in MR-guided or MR-assisted surgical procedures.

As an alternative to stainless steel, positioning devices have been fabricated from titanium. For example, Bookwalter clamps for interventional MR use have also been fabricated from titanium. While devices fabricated from titanium are not affected by the magnetic fields of the MR scanner and are therefore MR-safe, they are not MR-compatible. Titanium devices also do not address the issues noted above in regard to electrical conductivity.

Another disadvantage of devices fabricated from titanium is their high cost.

Hence, a surgical guide which is both MR-safe and MR-compatible is needed. It is also desirable to perform interventional surgical procedures in the operative environment of other imaging modalities such as X-Ray and CT and Fluoroscopic imaging systems. A compatible device in these environments should be unaffected by and substantially transparent to the imaging system. Such devices should allow the trajectory of the surgical tool be readily adjusted while providing stable and accurate guidance. The guide should also be unobtrusive, easy to use, and usable with a variety of surgical tools.

SUMMARY OF THE INVENTION

The present invention is directed to a support apparatus that satisfies the need to provide a surgical guide which is (i) MR-safe and MR-compatible and/or (ii) X-Ray/CT transparent in the operative environment of an imaging device. The support apparatus allows the trajectory of the surgical tool be readily adjusted while providing stable and accurate guidance for use with a variety of surgical tools. A support apparatus having the features of the present invention comprises means for supporting the surgical instrument. The support means is adapted to position the surgical instrument along a desired trajectory and is made of material compatible for use in the operative environment of the imaging device. A means for securing the position and trajectory of the surgical instrument operatively engages the support means and is also made of material compatible for use in the operative environment of the imaging device.

In accordance with a more limited aspect of the present invention, the apparatus includes a first member having a first aperture extending through guide member. The first aperture is adapted to receive the surgical instrument. A second member has a second aperture and is adapted to receive the surgical instrument. The relative position of the first and second members is selectively adjustable to vary the relative positions of the first and second apertures thereby securing the surgical instrument.

In accordance with a more limited aspect of the present invention, the first member has a circular counterbore eccentrically located with respect to the first aperture. The second member is adapted to be rotatably received in the counterbore. The second aperture is located eccentrically with respect to the counterbore when the second member is received in the counterbore.

In a more limited aspect of the present invention, the material compatible for use in the operative environment of the imaging device is a polymer material and in a more limited aspect, the polymer material is polycarbonate, polyetherimide, polyacetal, polyphenylsulfone or polyarylethersulfone.

In accordance with another limited aspect of the invention, the support means includes a plurality of markers placed at known locations with respect thereto. The markers are adapted to provide signals indicative of their position in the operative environment of the imaging device.

In accordance with another aspect of the present invention, an apparatus for securing an instrument in a support assembly comprises a first member having a first aperture adapted to receive the instrument. A second member has a second aperture extending therethrough and is adapted to receive the instrument. The relative position of the first and second members is selectively adjustable to vary the relative positions of the first and second apertures thereby securing the surgical instrument.

In accordance with another aspect of the present invention an apparatus for positioning a surgical instrument in the operative environment of an MR imaging system comprises a surgical instrument guide adapted to receive and position the surgical instrument. A magnetic resonance RF coil is mounted to the surgical instrument guide.

In accordance with a more limited aspect of the invention, the surgical instrument guide is made of material compatible for use in the operative environment of the MR imaging system.

In accordance with yet another more limited aspect of the invention the RF coil is adapted to allow the surgical instrument to pass through the RF coil.

In accordance with another aspect of the invention, an apparatus for supporting a surgical instrument in the operative environment of an imaging device comprises a member made of polymer material having spherical surface including a bore extending through the member along its diameter. A grip made of polymer material is included that has a grip surface defining an aperture adapted to receive the member for rotatable movement within the aperture. The grip extends around the member in a circumferential path and has a gap in the circumferential path. A fastener made of polymer material is operatively connected to the grip and is adjustable to change the size of the gap thereby adjusting the compressive force applied to the received member in the grip.

In accordance with a more limited aspect of the invention, the grip surface includes two axially spaced apart annular side segments, each of the side segments having an inner surface. The inner surface of each side segment is located a respective radius from the center of the grip aperture. The side segments are spaced apart by a central segment that has an inner surface located at a radius from the grip center greater than the side segments. Each of the side segments have an inner lip that contacts the received member.

In accordance with a more limited aspect of the present invention each of the components can be made of different polymer material than any of the other components.

One advantage of the present invention is that the instrument support device is both safe and compatible for use in the operative environment of an imaging device thereby allowing interventional surgical procedures to be carried out without affecting the image provided by the device.

Another advantage of the present invention is that it securely locks the surgical instrument within the support member without deforming the instrument.

Yet a further advantage of the present invention is that the support member is easily and more securely locked in the desired position.

The present invention provides the foregoing and other features hereinafter described and particularly pointed out in the claims. The following description and accompanying drawings set forth certain illustrative embodiments of the invention. It is to be appreciated that different embodiments of the invention may take form in various components and arrangements of components. These described embodiments being indicative of but a few of the various ways in which the principles of the invention may be employed. The drawings are only for the purpose of illustrating a preferred embodiment and are not to be construed as limiting the invention.

BRIEF DESCRIPTION OF THE DRAWINGS

The foregoing and other features and advantages of the present invention will become apparent to those skilled in the art to which the present invention relates upon consideration of the following detailed description of a preferred embodiment of the invention with reference to the accompanying drawings, wherein:

FIG. 1 is a partial exploded perspective view in accordance with one embodiment of the present invention;

FIG. 2 is a perspective view of a guide assembly for use in the embodiment shown in FIG. 1;

FIG. 5 is a perspective view of a pivot ball for use in the guide assembly;

FIG. 6 is a sectional view of the pivot ball taken along the line 6—6 in FIG. 5;

FIGS. 8a, 8b, 8c are perspective and plan views of a locking collar for use with the surgical tool collar in FIGS. 7a,b,c;

DETAILED DESCRIPTION

Figure 3A:
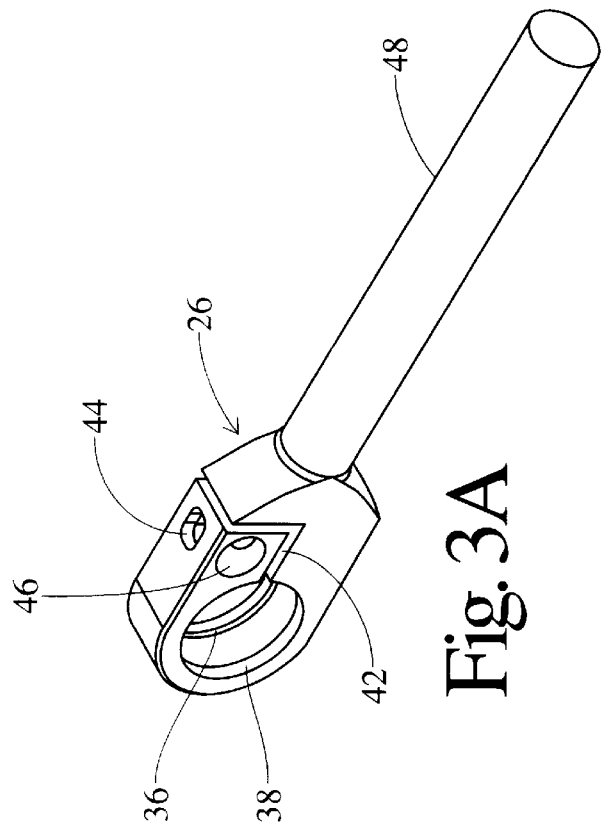
FIGS. 3a, 3b are perspective and plan views of a portion of the guide assembly shown in FIG. 2.

With reference to FIG. 1, an apparatus 1 for use as a surgical guide includes a post 12, a rod clamp assembly 14, and a guide assembly 16. The post 12 includes a jam nut 18 having threaded ends 20 and spokes 22. The rod clamp assembly 14 permits the relative positions of the post 12 and the guide assembly 16 to be adjusted in the directions indicated by the arrows. Tightening a hand screw 24 allows the guide assembly 16 to be fixed in a desired position. As described more fully below, the guide assembly 16 is adapted to receive inserts such as a needle collar 56 and locking collar 70 (shown in exploded view).

With reference to FIG. 2, the guide assembly 16 including a grip 26, a barrel nut 28 a hand screw 30 and a pivot ball 32. Upon tightening the hand screw 30, the position and trajectory of the surgical instrument is held firmly in place with the components of the guide assembly 16.

Figure 3B:
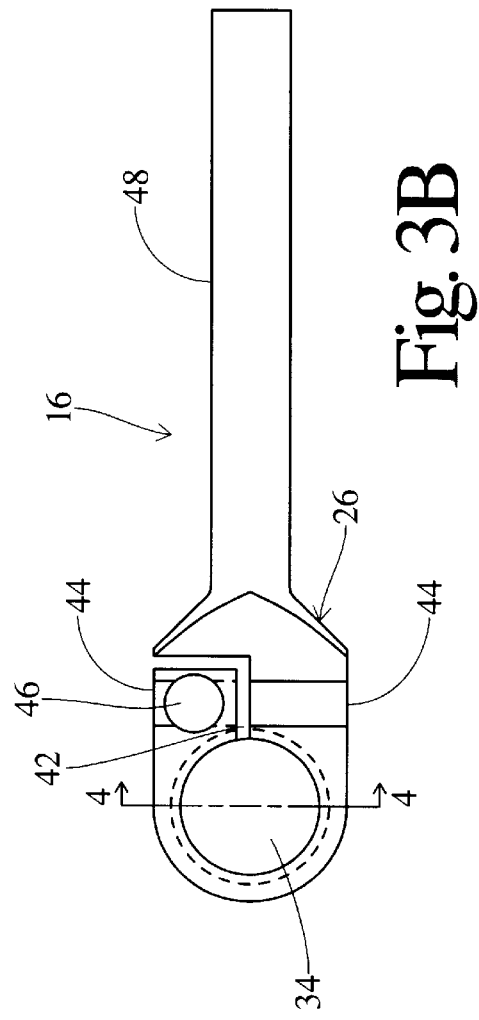
Figure 4:
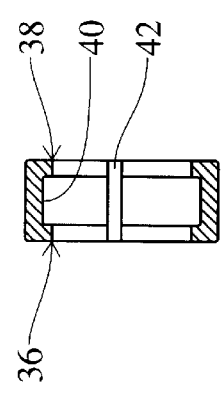
FIG. 4 is a sectional view of a grip along the line 4—4 in FIG. 3b.

As can best be seen in FIGS. 3a and 3b, the grip 26 includes a generally circular aperture 34 for receiving the pivot ball 32. With particular reference to FIG. 4, a first interior surface 40 of the pivot aperture 34 has a diameter greater than that of the pivot ball 32. First 36 and second 38 lips define diameters smaller than that of the pivot ball 32. During assembly, the pivot ball is pressed into the pivot aperture 34, after which the pivot ball 32 is retained in the pivot aperture 34. Preferably, the diameters defined by the lips 36 and 38 are slightly smaller than of the corresponding portions of the pivot ball 32 such that, while the pivot ball cannot be translated within the aperture 34, it is freely rotatable therein.

The grip 26 also includes a screw aperture 44 for receiving the hand screw 30 and a nut aperture 46 for receiving the barrel nut 28. The barrel nut 28 is generally cylindrical and includes a threaded through hole (not shown). The through hole is located so that, when the barrel nut is placed within the nut aperture 46, the barrel nut 28 may be rotated about its longitudinal axis until the through hole is coincident with the screw aperture 44. Threads on the hand screw 30 engage the barrel nut 28. A gap 42 allows the diameter of the pivot aperture 34 to be varied. In particular, tightening the hand screw 30 applies a compressive force across the gap 42, thereby reducing the diameter of the aperture 34. The guide assembly 16 includes a cylindrical handle portion 48 which engages the rod clamp 14.

With reference to FIGS. 5 and 6, the pivot ball 32 is generally spherical in shape. A ball aperture 50 extends through the diameter of the of the pivot ball 32. First 52a and second 52b flat surfaces are orthogonal to the longitudinal axis of the ball aperture 50. Threads 54 are located at the end the ball aperture 50 near the first flat surface 52a.

Figure 7A:
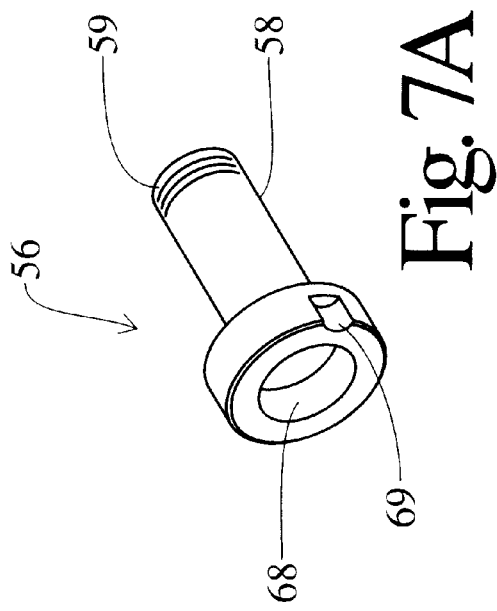
FIGS. 7a, 7b, 7c are perspective and plan views of a surgical tool guide collar for use in the pivot ball.
Figure 7C:
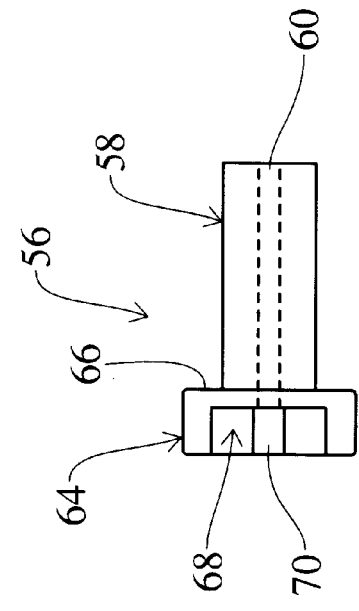
Figure 7B:
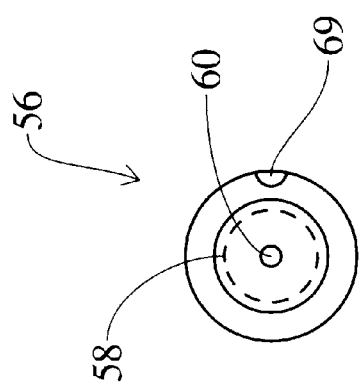

Various inserts may be received in the ball aperture 50. With reference to FIGS. 7a, 7b, and 7c a needle collar 56 which is particularly adapted for use with a biopsy needle includes a cylindrical insert portion 58 which is received in the ball aperture 50. Threads 59 on the insert portion 58 engage the threads 54 in the ball aperture 50 such that the needle collar 56 may be held firmly in place. The needle collar 56 includes a guide aperture 60 located at the center of the cylindrical insert portion 58. The guide aperture 60, which defines a guide axis, has a diameter appropriate for the biopsy needle to be used. The upper end 64 of the needle collar 56 has a diameter larger than that of the insert portion 58 and defines a shoulder 66. The upper end 64 also includes a counterbore 68 which is eccentric to the guide aperture 60. Preferably, the amount of eccentricity is approximately one-tenth the diameter of the guide aperture 60. Thus, for example, for a guide aperture 60 having a diameter of 1.95 mm, the counterbore 68 is eccentric by 0.2 mm. A notch 69 indicates the direction of eccentricity.

With reference to FIGS. 8a, 8b, and 8c, a locking collar 70 includes a cylindrical insert portion 72 which is adapted to be received in the counterbore 68 of the needle guide 56, preferably with a slight clearance fit. The locking collar 70 may also be rotatably attached within the counterbore 68, for example by way of appropriate tapers, mounting tabs, mounting lips, or the like. Preferably, however, the locking collar 70, even if rotatably attached, is readily removable from the needle guide 56.

The locking collar 70 includes a locking aperture 74 which is eccentric to the insert portion, preferably by approximately one-tenth the diameter of the locking aperture 74. Thus, for a locking aperture 74 having a diameter of 1.95 mm, the locking aperture 74 is eccentric by 0.2 mm. The upper end 76 of the locking collar 70 has a diameter larger than that of the insert portion 72 and defines a shoulder 78. A notch 80 defines the direction of eccentricity.

Other inserts are also contemplated. For example, a wand collar is adapted to receive a surgical device such as a probe or wand used in connection with an image guided surgery system. The wand collar is similar to the to the needle collar 56 shown in FIGS. 7a, 7b, and 7c, although the guide aperture 60 sized to accept the desired probe. Similarly, collars adapted to receive other surgical tools, such as Kelly coagulators, drills, drill sheaths, and the like may readily be implemented. These collars may also be used with an appropriate locking collars, with the locking aperture configured to accept the desired tool. In a preferred embodiment, however, collars for use with surgical wands and Kelly coagulators are not eccentric as described above.

While the guide apertures have been described as having a circular cross-sections, other cross sections may also be implemented, for example where it is desirable to retain a tool having a particular rotational sense. In this way, rotation of the tool within the guide aperture may be prevented. The apparatus may also be used in connection with tools for retracting tissue, such as brain spatulas. While the direction of eccentricity has been described as indicated by notches 69, 80, it will be appreciated the indication can be made by other means, for example markings, grooves, protrusions, geometrically distinct features, or the like.

The guide apparatus 1 is preferably fabricated from materials such as polymers which demonstrate the desired MR-safety and MR-compatibility and/or X-Ray/CT compatible while providing the necessary physical properties. In a preferred embodiment for MR imaging modalities, the post 12 and rod clamp 14 are fabricated from 30% glass filled polycarbonate, for example as marketed under the trade name Ultem 2300 G. E. Plastics of Pittsfield, Mass. Another suitable material is marketed under the trade name Zelux M-GF30 by Westlake Plastics of Lennie, Pa. An embodiment that is also X-Ray/CT compatible is fabricated without glass filling and may be made of the same material as the grip 26 and pivot ball 32 which are fabricated from polyetherimide, for example as marketed under the trade name Ultem 1000 by G. E. Plastics of Pittsfield, Mass. The hand screw 30 and barrel nut 28 are preferably fabricated from polyphenylsulfone, also known as polyarylethersulfone, for example as marketed under the trademark Radel R by Amoco Performance Products of Atlanta, Ga. Another suitable material is polyacetal, for example as marketed under the trade name Delrin by E.I. DuPont of Wilmington, Del. The various insert collars are preferably fabricated from polyphenylsulfone marketed under the trademark Radel R described above.

Other materials having suitable physical properties, particularly relatively high strength and stiffness, biocompatibility, and ease of sterilization, may be substituted. The materials used for the grip 26 and pivot ball 32 preferably have relatively high coefficients of friction, whereas the materials used for the hand screw 30 and barrel nut 28 have relatively low frictional coefficients. The guide apparatus 1 may also be fabricated from materials selected for their transparency to x-radiation where it desirable to use the apparatus 1 in connection with equipment such as CT scanners, radiographic equipment, or fluoroscopic equipment.

In operation, the post 12 of the guide apparatus 1 is screwed into a suitable structure, for example the bed of an MR scanner or other imaging device or a stationary scanner portion. The surgeon selects an appropriate collar, for example the wand collar described above. The collar is inserted into the pivot aperture 50 and tightened such that the threads on the collar engage the threads 54 in the pivot aperture and the shoulder 66 of the collar 56 is seated on the second surface 52b of the pivot ball 32. Thus, the collar is held firmly in place with respect to the pivot ball 32.

With the hand screw 30 loosened, the pivot ball 32 is freely rotatable in relation to the grip 26. The surgeon inserts a tool, such as a probe which is trackable by the image guided surgery system, into the guide aperture of the collar. The orientation of the tool is then adjusted, for example, by placing the tip of the probe on the surface of the patient and adjusting the position and orientation of the probe until a desired trajectory is achieved. Of course, the position of the guide assembly 16 in relation to the patient may be adjusted as necessary using the rod clamp 14.

When the tool has been properly oriented, the hand screw 30 is tightened. The resultant compressive force acts across the gap 42 to reduce the diameter of the grip aperture 34. The inner edges of the lips 36, 38 engage the pivot ball 32 along substantially their entire circumference and further apply compressive forces on the pivot ball 32. As a result, only a small amount of torque on the hand screw 30 is sufficient to create a large clamping force on the pivot ball 32. Thus, the pivot ball 32 and hence the guide axis and tool are held firmly in place. Of course, the trajectory of the probe may be re-adjusted as necessary.

With the tool guide assembly 16 and the pivot ball 32 fixed in place, the guide apparatus may be used to guide the application of various tools in respect to the anatomy of the patient. For example, the first tool may be removed from the guide aperture and replaced with an alternate tool such as a drill sheath and an associated surgical drill. Again, however, the trajectory of the tools is maintained.

Various collars may also be inserted in the pivot ball 32. Thus, for example, the wand collar may be removed and replaced with the needle collar 56. The locking collar 70 may then be inserted into the counterbore 68 of the needle collar 56. With the locking collar 70 rotated so that its notch 80 is aligned with the notch 69 on the needle collar, the respective locking 74 and guide 60 apertures are in substantial alignment. The desired tool, for example a biopsy needle, may be freely inserted through the apertures and applied to the patient. When the tool reaches a desired depth, the locking collar 70 is rotated within the counterbore 68. The eccentricity associated with the locking collar 70 and the needle collar 56 causes a misalignment of the respective apertures 74 and 60, thereby locking the tool at the desired depth. Hence, the guide apparatus 1 may be used to assist in the application of various tools while maintaining a desired trajectory in relation to the patient.

As described above, it was assumed that one or more of the tools used in connection with the guide apparatus was trackable by an image guided surgery system. Alternatively, a position signaling device such as a plurality of infrared emitters may be mounted to the pivot ball 32. Because the position of the position signaling device in relation to the guide axis is known, the position and orientation of the pivot ball 32 may be tracked and adjusted without using a separate, trackable tool. Depending on the requirements of a particular localizer system, other position signaling devices, such as reflective elements, sonic or electromagnetic emitters or receivers, or the like may be used.

The position signaling device may also be mounted to the grip 26. While this configuration does not provide information as to the orientation of the pivot ball 32, information as to the position and orientation of the grip 26 is provided. Because the pivot ball 32 is rotatably retained within the grip 26, the position of a point along the guide axis, i.e. a point located at the center of the pivot ball 32, is known. This configuration may advantageously be used in conjunction with a tool having a position signaling device such as an infrared emitter which has a known position in relation to the tip of the tool. The position of tool emitter, in conjunction with the known location of the center of the pivot ball 32, can thus be used to uniquely define the location and orientation of the tool.

Markers analogous to those used to define fiducial points on the patient's anatomy may also be affixed to the pivot ball 32 or the grip 26. The guide may then be imaged using the scanner. Because the markers contain a substance visible in the image, the markers provide information as to the position of the pivot ball 32 or the grip 26. The guide may also be used in connection with a tool which is visible in a scanned image. The position of the tool can then be seen directly in relation to the image. The foregoing configurations are particularly advantageous when the guide apparatus and the patient are both fixed in position with respect to a common support.

The positioning apparatus may also include a mechanical gauge system or markings which provide the surgeon with a visible indication of the guide's position and orientation. Such a configuration is particularly advantageous where the guide apparatus is used with conventional stereotactic equipment.

Figure 9:
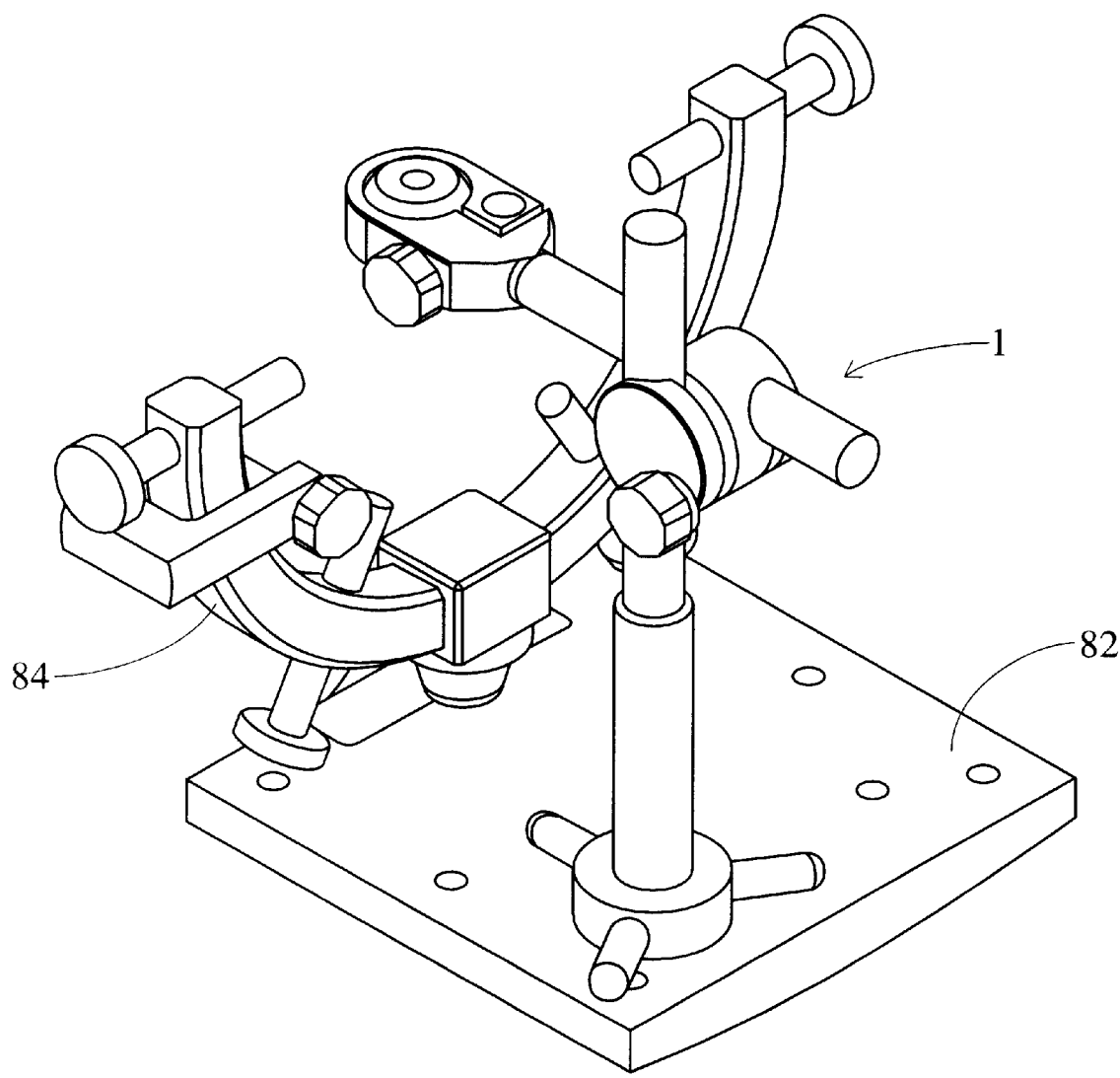
FIG. 9 is a perspective view of a guide apparatus in place for use with a patient head clamp.

With reference to FIG. 9, the guide apparatus 1 also includes an adaptor plate 82 which is attached to a suitable structure such as the scanning device's patient support. A patient patient holding device such as a head clamp 84 may also be attached to the adaptor plate 82. Such a configuration provides a readily transportable, rigid assembly. Alternately, the mounting post 12 may be adapted for attachment directly to the patient holding device 84.

Figure 10:
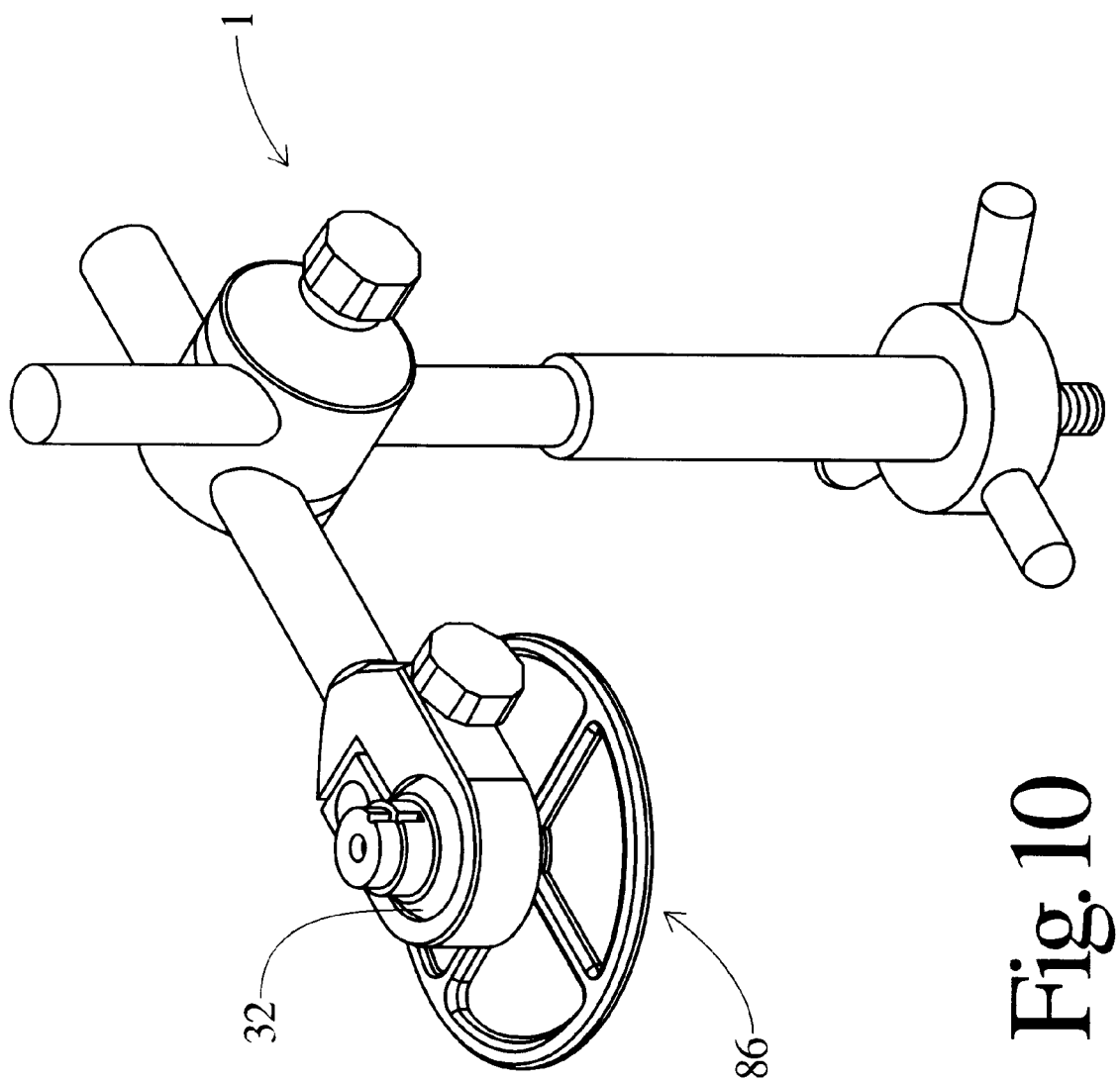
FIG. 10 is a perspective view of another embodiment of the present invention.

With reference to FIG. 10, the guide apparatus 1 may also include an RF coil 86 for transmitting radio frequency excitation signals which excite magnetic resonance, receiving radio frequency radio frequency magnetic resonance signals, or both. The RF coil may also additionally or alternately contain a spoiler coil.

In a preferred embodiment, the RF coil 86 a mounted to the underside of the pivot ball for movement therewith, for example by way of a threaded attachment. The coil 86 is preferably spaced apart from the pivot ball 32 and the grip 26 so as not to interfere with movement of the pivot ball 32. An aperture (not shown) in the RF coil 86 is coincident with the guide axis so as to allow insertion of a surgical tool therethrough. Alternately, the RF coil 86 may be mounted to the underside of the grip 26 for movement therewith.

When the surgical guide is in use, the RF coil 86 will ordinarily be located near the region of the patient's anatomy which is of particular interest, thereby facilitating imaging of the region when the patient and guide are placed in the imaging region of the MR scanner. By mounting the RF coil 86 to the pivot ball 32, the orientation of the coil with respect to the guide axis (shown as orthogonal in FIG. 10) is known.

Because the guide apparatus 1 may be positioned arbitrarily in relation to main magnetic field $B_0$ of the MR scanner, a multimode surface coil which supports the excitation and/or detection of resonance signals in three orthogonal modes is preferred. Such a coil is described in commonly assigned U.S. application Ser. No. 08/757,240, filed Nov. 27, 1996, entitled Arbitrary Placement Multimode Coil System for MR Imaging, now U.S. Pat. No. 5,757,289 issued on May 26, 1998 which is expressly incorporated in its entirety by reference herein.

While a particular feature of the invention may have been described above with respect to only one of the illustrated embodiments, such features may be combined with one or more other features of other embodiments, as may be desired and advantageous for any given particular application.

From the above description of the invention, those skilled in the art will perceive improvements, changes and modification. Such improvements, changes and modification within the skill of the art are intended to be covered by the appended claims.

What is claimed is:

1. An apparatus for supporting a surgical instrument in the operative environment of an imaging device, the apparatus comprising:

means for supporting the surgical instrument in a desired position along a desired trajectory, the means for supporting including a first member having a first aperture extending therethrough adapted to receive the surgical instrument and a second member having a second aperture extending therethrough, the second aperture adapted to receive the surgical instrument, the relative positions of the first and second members being selectively adjustable to vary the relative position of the first and second apertures thereby securing the surgical instrument; and means for securing the means for supporting.

2. The apparatus of claim 1 wherein the means for supporting and the means for securing are comprised of material compatible for use in the operative environment of the imaging device.

3. The apparatus of claim 2 wherein the surgical instrument is a biopsy needle and the first and second apertures are adapted to receive the biopsy needle.

4. The apparatus of claim 2 wherein the first member has a circular counterbore at one end of the first aperture, the counterbore is eccentrically located with respect to the first aperture, and the second member being adapted to be rotatably received in the counterbore of the first member, the second aperture located eccentrically with respect to the counterbore when the second member is received therein.

5. The apparatus of claim 2 wherein the material compatible for use in the operative environment of the imaging device is a polymer material.

6. The apparatus of claim 5 wherein the polymer material is polycarbonate, polyetherimide, polyacetal, polyphenylsulfone or polyarylethersulfone.

7. The apparatus of claim 1 wherein the means for supporting includes a plurality of markers placed at known locations with respect thereto, the markers being adapted to provide signals indicative of their position in the operative environment of the imaging device.

8. An apparatus for securing an instrument in a support assembly, the apparatus comprising:

a first member having a first aperture extending therethrough, the first aperture adapted to receive the surgical instrument; and a second member having a second aperture extending therethrough, the second aperture adapted to receive the surgical instrument, the relative position of the first and second members selectively adjustable to vary the relative position of the first and second apertures, thereby securing the surgical instrument.

9. The apparatus of claim 8 wherein the first member includes a counterbore at one end of the first aperture and the counterbore is eccentrically located with respect to the first aperture.

10. The apparatus of claim 9 wherein the amount of eccentricity of the counterbore is approximately one tenth the diameter of the first aperture.

11. The apparatus of claim 9 wherein the second member is adapted to be movably received in the counterbore of the first member and the second aperture is located eccentric to the center of the second member.

12. The apparatus of claim 11 wherein the amount of eccentricity of the second aperture is approximately one tenth the diameter of the second aperture.

13. An apparatus for supporting a surgical instrument in the operative environment of an imaging device, the apparatus comprising:

a member made of polymer material having a spherical surface, the member including a bore extending through the member along its diameter, a grip made of polymer material having a grip surface defining an aperture adapted to receive the member for movement within the aperture, the grip extending around the member in a circumferential path, the grip having a gap in the circumferential path; and a fastener made of polymer material operatively connected to the grip, the fastener adapted to change the size of the gap and adjust the compressive force applied to the received member in the grip.

14. The apparatus of claim 13 wherein the grip surface includes two axially spaced apart annular side segments, each of the side segments having an associated inner surface, the inner surface of each side segment located a respective radius from the center of the grip aperture, the side segments spaced apart by a central segment having an inner surface with a radius greater than that of each of the side segments thereby forming on each of the side segments an associated inner lip that contacts the received member.

15. The apparatus of claim 13 including a guide collar made of polymer material having a guide aperture extending through the guide collar, the guide collar includes a counterbore at one end of the guide collar, the counterbore is eccentrically located with respect to the guide aperture, the guide collar is adapted to be securely received in the bore; and a locking collar made of polymer material is adapted to be movably received in the counterbore of the guide collar, the locking collar having a locking aperture, the locking aperture is located eccentric to the counterbore when received in the counterbore.

16. The apparatus of claim 15 including notches located on each of the guide collar and locking collar indicative of the orientation of the eccentricity of each of the respective guide collar and locking collar.

17. The apparatus of claim 15 wherein the amount of eccentricity of the counterbore is approximately one tenth the diameter of the guide aperture.

18. The apparatus of claim 17 wherein the amount of eccentricity of the locking aperture is approximately one tenth the diameter of the locking aperture.

19. The apparatus of claim 13 wherein the polymer material is polycarbonate, polyetherimide, polyacetal, polyphenylsulfone or polyarylethersulfone.

20. The apparatus of claim 19 wherein at least one of the member, guide collar, locking collar, grip and fastener are made of different polymer material than at least one other of the member, guide collar, locking collar, grip and fastener.

21. The apparatus of claim 13 wherein the grip includes a plurality of markers placed at known locations relative thereto, the markers being adapted to providing signals indicative of their position in the operative environment of the imaging device.

22. The apparatus of claim 13 wherein the member includes a plurality of markers placed at known locations relative thereto, the markers being adapted to providing signals indicative of their position in the operative environment of the imaging device.

23. The apparatus of claim 13 including a magnetic resonance RF coil mounted to at least one of the member and the grip.

* * * * *